(12) United States Patent
Kawano et al.

(10) Patent No.: US 8,702,591 B2
(45) Date of Patent: Apr. 22, 2014

(54) CAPSULE MEDICAL APPARATUS

(75) Inventors: Hironao Kawano, Hino (JP); Masaki Takahashi, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 1333 days.

(21) Appl. No.: 11/653,168

(22) Filed: Jan. 12, 2007

(65) Prior Publication Data
US 2009/0005639 A1  Jan. 1, 2009

(51) Int. Cl.
 A61B 1/00 (2006.01)
 A61B 1/04 (2006.01)
 A61B 1/06 (2006.01)

(52) U.S. Cl.
 USPC ........... 600/117; 600/103; 600/109; 600/118; 600/160; 600/178

(58) Field of Classification Search
 USPC ......... 600/101, 109, 114–118, 423, 470, 103, 600/160, 168
 See application file for complete search history.

(56) References Cited

U.S. PATENT DOCUMENTS

| | | | |
|---|---|---|---|
| 6,240,312 B1 * | 5/2001 | Alfano et al. | 600/476 |
| 6,524,608 B2 | 2/2003 | Ottoboni et al. | |
| 7,160,258 B2 * | 1/2007 | Imran et al. | 600/593 |
| 7,192,397 B2 * | 3/2007 | Lewkowicz et al. | 600/160 |
| 7,316,647 B2 | 1/2008 | Kimoto et al. | |
| 2003/0181788 A1 | 9/2003 | Yokoi et al. | |
| 2003/0216622 A1 * | 11/2003 | Meron et al. | 600/300 |
| 2004/0249291 A1 | 12/2004 | Honda et al. | |
| 2005/0020880 A1 * | 1/2005 | Miyake et al. | 600/121 |
| 2005/0049461 A1 | 3/2005 | Honda et al. | |
| 2005/0085696 A1 | 4/2005 | Uchiyama et al. | |
| 2005/0171398 A1 | 8/2005 | Khait et al. | |
| 2006/0056828 A1 * | 3/2006 | Iddan et al. | 396/14 |

(Continued)

FOREIGN PATENT DOCUMENTS

| | | |
|---|---|---|
| EP | 1 652 466 A1 | 5/2006 |
| JP | 2003-038424 A | 2/2003 |

(Continued)

OTHER PUBLICATIONS

U.S. Office Action dated Jan. 14, 2011.

(Continued)

Primary Examiner — Philip R Smith
Assistant Examiner — Rynae Boler
(74) Attorney, Agent, or Firm — Scully, Scott, Murphy & Presser, P.C.

(57) ABSTRACT

A capsule medical apparatus includes a capsule housing 3 having a protruded portion on a long axis at one end. The protruded portion is on a straight line lvm connecting a center of buoyancy Pv and a center of gravity Pm when the capsule housing is in liquid 7 in a body cavity, and the protruded portion is formed so that at least one straight line is present which passes a point Pf at which buoyant moment produced by buoyancy acting on the center of buoyancy Pv and gravitational moment produced by gravity acting on the center of gravity Pm are balanced and which intersects perpendicularly with an outer surface of the protruded portion. The inclined posture allows the capsule housing to receive a large fluid resistance against the liquid 7. Moreover, the capsule endoscope 1 can easily move along the flow of the liquid 7 because the capsule endoscope 1 is in the point contact state with the inner wall surface 2a.

20 Claims, 13 Drawing Sheets

(56) References Cited

U.S. PATENT DOCUMENTS

| | | | |
|---|---|---|---|
| 2007/0100208 A1* | 5/2007 | Lewkowicz et al. | 600/160 |
| 2007/0129624 A1 | 6/2007 | Gilad et al. | |
| 2007/0221233 A1* | 9/2007 | Kawano et al. | 128/899 |
| 2007/0260105 A1 | 11/2007 | Uchiyama et al. | |
| 2008/0015411 A1 | 1/2008 | Kimoto et al. | |
| 2008/0084478 A1* | 4/2008 | Gilad et al. | 348/207.99 |
| 2008/0242928 A1* | 10/2008 | Kawano et al. | 600/109 |

FOREIGN PATENT DOCUMENTS

| | | | | |
|---|---|---|---|---|
| JP | 2003210395 A | * | 7/2003 | A61B 1/00 |
| JP | 2004-073887 | | 3/2004 | |
| JP | 2005-334331 A | | 12/2005 | |
| KR | 2006-0005391 | | 1/2006 | |
| KR | 2006-0013518 | | 2/2006 | |
| KR | 2006-0030051 | | 4/2006 | |
| WO | WO 02/095351 A2 | | 11/2002 | |
| WO | WO 2004/058043 A2 | | 7/2004 | |
| WO | WO 2005/060348 A2 | | 7/2005 | |
| WO | WO 2005062717 A2 | * | 7/2005 | A61B 1/00 |

OTHER PUBLICATIONS

Japanese Office action dated Feb. 7, 2012 from corresponding Japanese Patent Application No. JP 2009-522469 together with English language translation.

* cited by examiner

CAPSULE MEDICAL APPARATUS

BACKGROUND OF THE INVENTION

1. Field of the Invention

The present invention relates to a capsule medical apparatus capable of moving in a stable posture in liquid introduced into a subject along a flow of the liquid, for example, and capable of performing an observation and medical practice such as obtaining an image inside the subject, for example.

2. Description of the Related Art

In recent years, in the field of endoscopes, there have been introduced capsule endoscopes provided with an imaging function and a wireless communication function. For the purpose of observation (examination), such a capsule endoscope is configured to sequentially image, using the imaging function, in an internal organ such as an esophagus, a stomach, or a small intestine (in a body cavity) along with peristalsis thereof, during an observation period after the capsule endoscope is taken into a patient being a subject (human body) from the mouth of the patient and until it is naturally eliminated from a living body of the patient.

It should be noted that, Patent Document 1 (International Publication WO 02/95351 Pamphlet (PCT National Publication No. 2004-529718)) discloses a technique suitable for an observation of a large intestine in which a capsule endoscope is taken with liquid to float in the liquid by setting the specific gravity of the capsule endoscope to be either the same as the liquid that surrounds the capsule endoscope, or one (1), which is the same as the specific gravity of water, thereby allowing the capsule endoscope to advance speedily in the body cavity to the large intestine. In addition, while only the proximity of the capsule endoscope can be observed when the capsule endoscope sticks to a wall surface of the body cavity, it is possible to ensure a field of view for observation and to observe everything according to Patent Document 1, because the capsule endoscope is made to float in the liquid for observation.

However, a problem has been noted that, when floating, the conventional capsule endoscope cannot move or stop along the flow of the liquid and a posture of the capsule endoscope becomes unstable, and therefore it is not possible to perform a desired observation or medical practice.

SUMMARY OF THE INVENTION

An object of the present invention is to provide a capsule medical device capable of moving, floating, and stopping along the flow of liquid introduced into a subject being tested, as well as capable of taking a desired posture in a stable manner.

A capsule medical apparatus according to the present invention comprises a capsule housing having a protruded portion on a longitudinal axis at one end. The protruded portion is formed so that an outer surface of the protruded portion intersects perpendicularly with a first straight line. The first straight line substantially intersects with a second straight line connecting a center of buoyancy and a center of gravity when the capsule housing is in liquid in a body cavity. The first straight line and the second straight line substantially intersect at a point where buoyant moment produced by buoyancy acting on the center of buoyancy and gravitational moment produced by gravity acting on the center of gravity are substantially balanced.

In the capsule medical apparatus according to the present invention, specific gravity of the capsule medical apparatus is a proximity value of specific gravity of the fluid.

In the capsule medical apparatus according to the present invention, when the gravity is greater than the buoyancy, a distance between the point at which the moments are balanced and the center of buoyancy is larger than a distance between the point at which the moments and the center of gravity, and the protruded portion is brought into contact with an inner wall of the body cavity downward in a vertical direction of the point at which the moments are balanced.

In the capsule medical apparatus according to the present invention, when the gravity is smaller as compared to the buoyancy, a distance between the point at which the moments are balanced and the center of buoyancy is smaller than a distance between the point at which the moments and the center of gravity, and the protruded portion is brought into contact with an inner wall of the body cavity upward in a vertical direction of the point at which the moments are balanced.

In the capsule medical apparatus according to the present invention, either the point at which the moments are balanced is positioned between an intersection of the straight line that intersects perpendicularly with the outer surface of the protruded portion and the protruded portion, and a center of curvature of the protruded portion at the intersection in a plane including the point at which the moments are balanced, the intersection, and the center of buoyancy, or the intersection is positioned between the point at which the moments are balanced and the center of curvature.

In the capsule medical apparatus according to the present invention, an acute angle formed by the first straight line that intersects perpendicularly with the outer surface of the protruded portion and the longitudinal axis is equal to or smaller than 80 degrees.

The capsule medical apparatus according to the present invention further comprises a fluid resistance portion having a resistance to the fluid that flows in the body cavity.

In the capsule medical apparatus according to the present invention, the fluid resistance portion is a fin provided on a surface of the capsule housing, and capable of producing a force in a direction to move away from an inner wall surface of the body cavity in response to a flow of the fluid.

In the capsule medical apparatus according to the present invention, the fluid resistance portion is a fin that produces a rotational motion about the longitudinal axis.

In the capsule medical apparatus according to the present invention, the capsule housing includes a first housing unit having an intersection of the first straight line that intersects perpendicularly with the outer surface of the protruded portion and the protruded portion, and a second housing unit having the fluid resistance portion, the first housing unit and the second housing unit are connected via a resilient member, energy which the fluid resistance portion receives is accumulated at the resilient member, and the capsule medical apparatus is separated from the inner wall surface of the body cavity using the accumulated energy.

In the capsule medical apparatus according to the present invention, both ends of the capsule housing in a longitudinal axis direction form a dome shape.

In the capsule medical apparatus according to the present invention, the capsule housing is provided with an imaging system on the other end of the protruded portion, the imaging system imaging an image in the body cavity.

In the capsule medical apparatus according to the present invention, the center of gravity is positioned at an eccentric position from the longitudinal axis of the capsule housing, and an imaging axis of the imaging system is provided at an angle with the longitudinal axis centering around a straight line perpendicular to a plane including the longitudinal axis and the center of gravity.

The capsule medical apparatus according to the present invention further comprises a rectifying portion that is provided on a surface of the capsule housing and rectifies a flow of the liquid.

The capsule medical apparatus according to the present invention further comprises a fluid resistance portion that is provided on a surface of the capsule housing and has the capsule medical apparatus turn about the longitudinal axis in response to a flow of the liquid.

The capsule medical apparatus according to the present invention further comprises a magnetic body, within the capsule housing, having magnetism that is substantially perpendicular to the longitudinal axis. The capsule housing turns about the longitudinal axis by rotating magnetic field applied from outside.

In the capsule medical apparatus according to the present invention, the protruded portion includes a flat portion, an intersection of the first straight line that intersects perpendicularly with the outer surface of the protruded portion and the protruded portion is at the flat portion.

In the capsule medical apparatus according to the present invention, the protruded portion includes a circular truncated cone plane portion, an intersection of the first straight line that intersects perpendicularly with the outer surface of the protruded portion and the protruded portion is at the circular truncated cone plane portion.

In the capsule medical apparatus according to the present invention, the capsule housing includes a body portion that is in a substantial cylindrical shape and whose center axis is parallel to the longitudinal axis, and a radius of curvature of the protruded portion at an intersection of the first straight line that intersects perpendicularly with the outer surface of the protruded portion and the protruded portion is greater than a diameter of the substantial cylindrical shape.

In the capsule medical apparatus according to the present invention, the protruded portion has a substantially oval spherical protruded shape that is connected to the substantial cylindrical shape, and the radius of curvature of the protruded portion increases gradually toward an end in a direction of the longitudinal axis.

In the capsule medical apparatus according to the present invention, the protruded portion has a substantially oval spherical protruded shape that is connected to the cylindrical shape, and the radius of curvature of the protruded portion decreases gradually toward an end in a direction of the longitudinal axis.

In the capsule medical apparatus according to the present invention, the capsule medical apparatus is in point contact with a body cavity inner wall surface at an intersection of the first straight line that intersects perpendicularly with the outer surface of the protruded portion and the protruded portion.

A capsule medical apparatus according to the present invention comprises a point contact portion having a protruded shape on a circumference of one end of a capsule housing having a body in a substantially cylindrical shape. Moment of the center of buoyancy and moment of the center of gravity are balanced so that the capsule medical apparatus takes a desired posture such that the capsule medical apparatus is brought into point contact with an inner wall surface of a body cavity at the point contact portion in liquid introduced into the body cavity, the moment of the center of buoyancy centering around an intersection of a straight line passing through a center of buoyancy and a center of gravity of the capsule housing and a vertical line passing through the point contact portion.

In the capsule medical apparatus according to the present invention, either the intersection is positioned between the point contact portion and a center of curvature of the point contact portion, or the point contact portion is positioned between the intersection and the center of curvature of the point contact portion.

In the capsule medical apparatus according to the present invention, an acute angle formed by the vertical line that passes the point contact portion and the longitudinal axis is equal to or smaller than 80 degrees.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

The following describes embodiments of a capsule medical apparatus according to the present invention in detail with reference to the drawings. In the following embodiments, a capsule endoscope with an imaging function is explained as an example of the capsule medical apparatus. The present invention is not limited to these embodiments, and various modifications may be implemented within the scope of the spirit of the present invention.

First Embodiment

Figure 1:
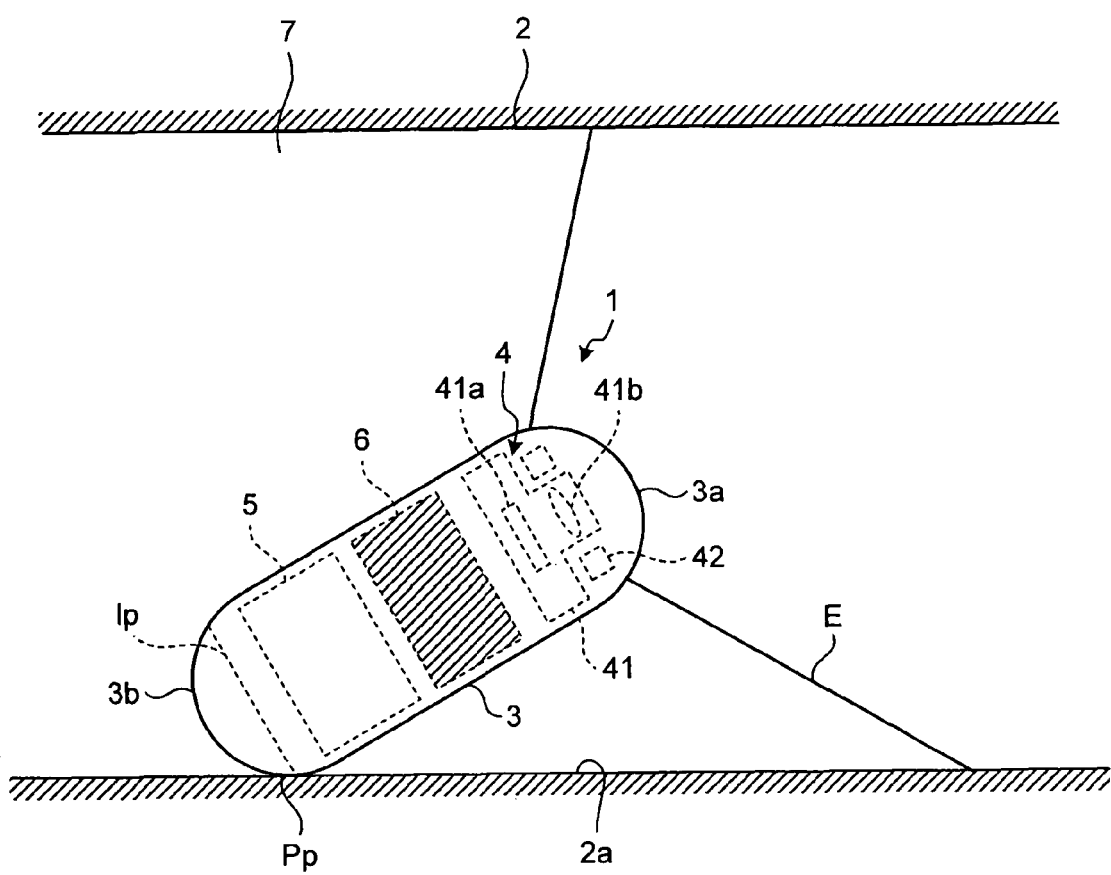
FIG. 1 shows a schematic construction of a first embodiment of a capsule endoscope according to the present invention.

FIG. 1 shows a schematic construction of one embodiment of a capsule endoscope according to the present invention. A capsule endoscope 1 includes a capsule housing 3 that may be introduced into a body cavity of a subject 2, an imaging optical system 4 disposed in the capsule housing 3 and capable of imaging in an anterior end direction, a circuit system unit 5 such as a control board disposed in the capsule housing 3, a circuit component, and a transmitting antenna, and a battery 6.

The size of the capsule housing 3 is such that it may be taken into the subject 2 through a mouth orifice thereof. A substantially hemispherical tip cover 3a that is either transparent or translucent is elastically fitted with a body cover 3b made of a colored material that blocks visible light and is shaped like a cylinder with a bottom, thereby forming a liquid-tight external casing.

Here, the capsule endoscope 1 according to the present invention obtains an image of a subject to be imaged, for example, an inner wall of a large intestine, as an internal image of the subject. The capsule housing 3 is configured so that the specific gravity of the capsule housing 3 including components housed therein is slightly higher than that of the liquid 7, and while the capsule housing 3 sinks in the liquid 7, a projection lp of the body cover 3b comes into point contact with an inner wall surface 2a of the body cavity downward in a vertical direction at a point Pp. As a result, the capsule housing 3 takes either a desired inclined posture in which a direction of a long axis thereof is inclined with respect to a horizontal direction or a vertical posture. The liquid 7 is transmissive of a wavelength of the imaging optical system 4 of the capsule endoscope 1, and may be drunk through the mouth orifice of the subject 2. An example used in this embodiment is drinking water or intestinal lavage fluid whose specific gravity is close to one (1). It should be noted that, in this embodiment, the specific gravity of the liquid 7 may be equal to or greater than one (1).

The battery 6 is a heavy component among the components housed in the capsule endoscope 1, and disposed substantially in a central portion in the capsule housing 3. It is possible to balance the weight mainly by varying the position of the battery 6, because the battery is a heavy component.

The imaging optical system 4 is constituted by an imaging unit 41 and an illumination unit 42. The imaging unit 41 is provided, along an axis center of the capsule housing 3, with an imaging device 41a, such as a CCD or CMOS imager, that images an image of the subject to be imaged as the internal image of the subject by receiving illuminating light from the illumination unit 42 reflected on the subject to be imaged, and an imaging lens 41b that has the imaging device 41a image an optical image of the subject to be imaged. The imaging unit 41 then obtains the image of the subject to be imaged as the internal image of the subject.

The illumination unit 42 is for illuminating an imaging field E of the imaging unit 41, and realized by a plurality of light sources such as LEDs that emit illuminating light for illuminating an imaging site of the subject to be imaged via the tip cover 3a. The plurality of LEDs are disposed around the imaging unit 41 centering the optical axis of the imaging unit 41 so as to cover an entire area of the imaging field E.

The imaging unit 41 is provided for the capsule endoscope housing 3 on a side not in contact with the inner wall. With this, it is possible to obtain a wider field of view in an intestinal tract having a wide space.

Figure 2:
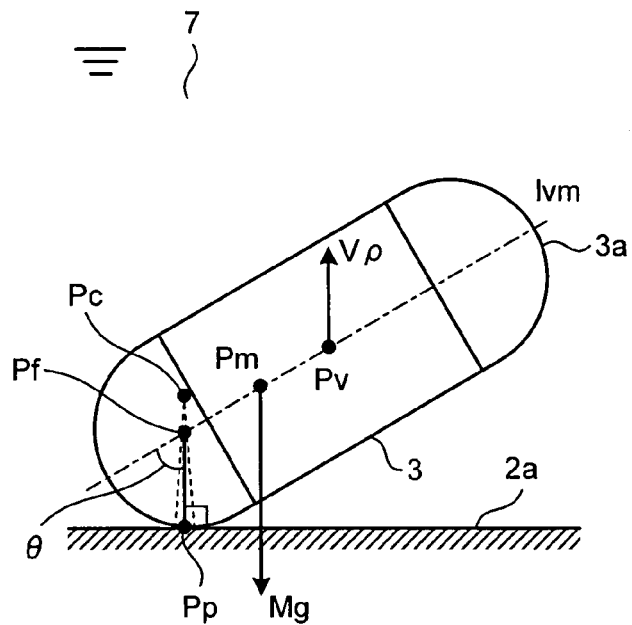
FIG. 2 is a diagram illustrating stability conditions for the capsule endoscope shown in FIG. 1 to take an inclined posture.

Next, referring to FIG. 2, conditions are explained under which the capsule endoscope 1 may stably take the inclined posture in a point contact state with the inner wall surface 2a of the body cavity downward in a vertical direction.

In FIG. 2, Pm represents a center of gravity of the capsule endoscope 1, and Pv represents a center of buoyancy (center of volume) of the capsule endoscope 1. Here, a straight line that passes Pm and Pv is indicated by lvm. Further, a point on lvm at which buoyant moment produced by buoyancy acting on the center of buoyancy and gravitational moment acting on the center of gravity are balanced is indicated as Pf. In other words, when Mg represents the gravity and Vρ represents the buoyancy, distance $PfPv$×buoyancy $V\rho$=distance $PfPm$×gravity $Mg$ is established. At this time, because the capsule endoscope 1 needs to sink to the inner wall surface 2a of the body cavity, the gravity Mg is required to be greater as compared to the buoyancy Vρ. Therefore, the distance PfPm is shorter as compared to the distance PfPv.

Here, the capsule endoscope 1 includes, out of any given lines passing through the point Pf, a line that perpendicularly intersects with the projection lp of the capsule endoscope 1, and an intersection of the line with the projection lp is taken as the point Pp. The capsule endoscope 1 having the point Pp as described above may maintain its posture in the point contact state at the point Pp with the inner wall surface 2a of the body cavity. Moreover, when the meeting of a straight line connecting the point Pp and the point Pf and the straight line lvm forms an acute angle θ, the long axis of the capsule keeps the inclined posture at an angle of 90°−θ with the horizontal plane. It should be noted that, while the long axis of the capsule endoscope 1 and the line lvm match each other in this example, the present invention is not limited to this example, and the same principle is established when the long axis and the line lvm do not match as in an example 3 which will be described later.

Further, a central position Pc is positioned along the straight line connecting the point Pp and the point Pf, and the central position Pc is a central position of curvature in a plane including the points Pv, Pf, and Pp at a surface of the point Pp. Therefore, a distance between the point Pp and the point Pc is a radius of curvature.

Although not shown here, when the moment due to the buoyancy produced in the capsule endoscope 1 is sufficiently greater than the moment due to the gravity, the posture of the capsule endoscope 1 is stabilized at an angle at which the line lvm becomes vertical (i.e., the moment due to the buoyancy and the moment due to the gravity are balanced). At this time, the moments centering the point Pf become zero (0) both for the moment due to the buoyancy and the moment due to the gravity.

Figure 3:
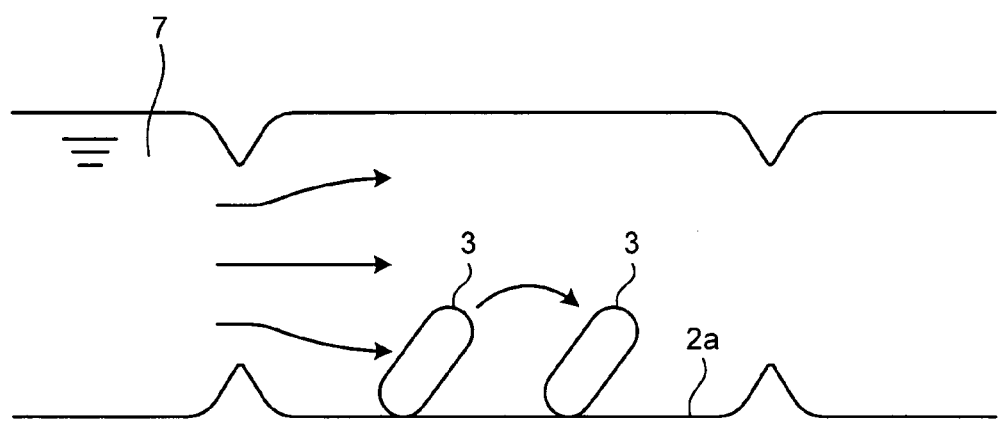
FIG. 3 is an illustrative diagram showing a moving state of the capsule endoscope shown in FIG. 1 in a large intestine.

When the capsule endoscope 1 can maintain the inclined posture or the vertical posture with respect to the inner wall surface 2a of the body cavity in a stable manner, a fluid resistance against the liquid 7 becomes greater as shown in FIG. 3, and the capsule endoscope 1 can easily move along the flow of the liquid 7 because the capsule endoscope 1 is in the point contact state with the inner wall surface 2a of the body cavity. Further, because the capsule can float easily, it is possible to obtain an image at a center of a tube and improve observability. In this case, the capsule endoscope 1 maintains substantially the inclined posture or the vertical posture in a stable manner, it is possible to obtain an image of an entire or a desired wall in the body cavity. Note that, when the capsule endoscope 1 takes a horizontal posture and is in a line contact state with the inner wall surface 2a of the body cavity, it is not possible to obtain sufficient fluid resistance against the liquid 7, thereby decreasing mobility and flotation of the capsule endoscope 1. In particular, in the body cavity having a large tube diameter such as a large intestine, the flow of the liquid 7 is faster around the tube center than near the tube wall, and therefore, when the capsule endoscope 1 is in the line contact state with the wall, the mobility and the flotation are decreased.

Here, the capsule endoscope 1 shown in FIG. 2 is in point contact with the inner wall surface 2a of the body cavity downward in the vertical direction. However, as shown in FIG. 4, the capsule endoscope 1 may be in point contact with the inner wall surface 2b of the body cavity upward in the vertical direction.

The stability conditions of the capsule endoscope 1 in this case are different from those of the capsule endoscope 1 shown in FIG. 2 in that, firstly, a gravity Mg of the capsule endoscope 1 is smaller as compared to a buoyancy Vρ of the capsule endoscope 1. Further, based on the balance of the moments, the distance PfPm is longer than the distance PfPv. Moreover, when the moment due to the gravity produced in the capsule endoscope 1 is sufficiently greater than the moment due to the buoyancy, the posture of the capsule endoscope 1 is stabilized at an angle at which the line lvm becomes vertical (i.e. the moment due to the buoyancy and the moment due to the gravity are balanced). At this time, the moments centering the point Pf become zero (0) both for the moment due to the buoyancy and the moment due to the gravity.

Figure 4:
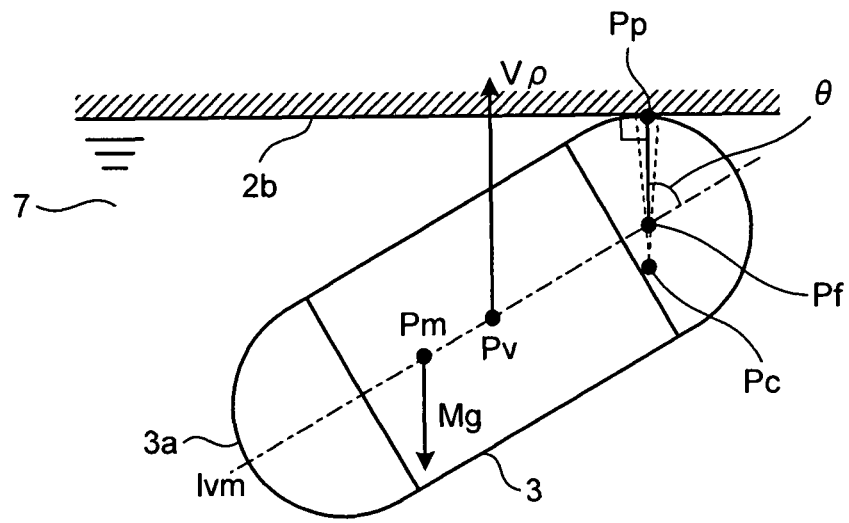
FIG. 4 is a diagram illustrating the stability conditions for the capsule endoscope to take the inclined posture, when the capsule endoscope is in a point contact with an inner wall of a body cavity upward in a vertical direction.

In the meantime, although the above mentioned capsule endoscopes 1 as shown in FIG. 2 or FIG. 4 can maintain the point contact state respectively with the inner wall surface 2a or 2b of the body cavity, it is possible to maintain the inclined posture or the vertical posture even more stably by either positioning the point Pf between the points Pp and Pc, or positioning the points Pp between the points Pf and Pc.

Figure 5:
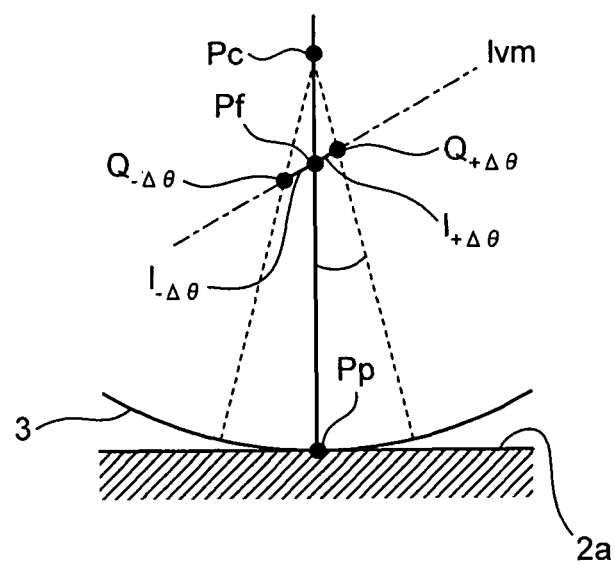
FIG. 5 is a diagram illustrating a size of a radius of curvature that further stabilizes the capsule endoscope shown in FIG. 2.

FIG. 5 shows a proximity of the point contact portion of the capsule endoscope shown in FIG. 2, and in the above mentioned state in which the moments of the gravity and the buoyancy are balanced, it is possible to stabilize the posture like a tumble doll weighted at the base, by either positioning the point Pf between the points Pp and Pc, or positioning the points Pp between the points Pf and Pc, even when a disturbance ($-\Delta\theta$, $+\Delta\theta$) is added.

In FIG. 5, when there is a displacement of $-\Delta\theta$, that is, when the line lvm of the capsule endoscope 1 shifts in the vertical direction, a displacement in moment α (moment in the vertical direction−moment in the horizontal direction) becomes as follows with a displacement in length $1_{-\Delta\theta}$ on the line lvm.

$$\alpha = (PvPf + 1_{-\Delta\theta}) \times V\rho - (PmPf + 1_{-\Delta\theta}) \times Mg$$

$$= 1_{-\Delta\theta} \times (V\rho - Mg) < 0$$

Therefore, a moment is produced in a direction in which the acute angle θ increases, i.e. the horizontal direction, and negates the displacement of $-\Delta\theta$. In other words, a restoring force is produced.

Similarly, when there is a displacement of $+\Delta\theta$ (displacement in the horizontal direction), the displacement in moment α is as follows.

$$\alpha = (PvPf - 1_{+\Delta\theta}) \times V\rho - (PmPf - 1_{+\Delta\theta}) \times Mg$$

$$= 1_{+\Delta\theta} \times (Mg - V\rho) > 0$$

In this case also, the displacement of $+\Delta\theta$ is negated, i.e. the restoring force is produced. Therefore, the restoring force is produced when one of the disturbances $-\Delta\theta$ and $+\Delta\theta$ is produced, and the inclined posture of the capsule endoscope 1 may be kept even more stably.

Figure 6:
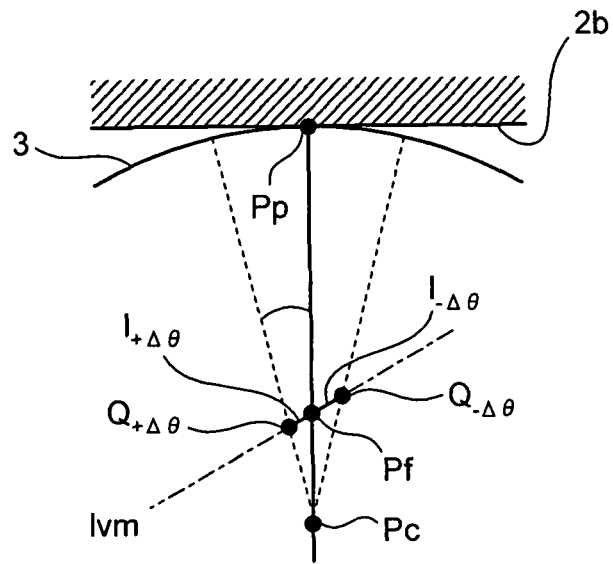
FIG. 6 is a diagram illustrating a size of a radius of curvature that further stabilizes the capsule endoscope shown in FIG. 4.

Furthermore, the same applies when the capsule endoscope 1 is in point contact with the inner wall surface 2b of the body cavity upward in the vertical direction as shown in FIG. 4. That is, when there is the displacement of $-\Delta\theta$ (displacement in the vertical direction) in FIG. 6, the displacement in moment α is as follows.

$$\alpha = (PvPf + 1_{-\Delta\theta}) \times Mg - (PmPf + 1_{-\Delta\theta}) \times V\rho$$

$$= 1_{-\Delta\theta} \times (Mg - V\rho) < 0$$

Therefore, a moment is produced in a direction in which the acute angle θ increases, i.e. the horizontal direction, and negates the displacement of $-\Delta\theta$. In other words, a restoring force is produced.

Similarly, when there is a displacement of $+\Delta\theta$ (displacement in the horizontal direction), the displacement in moment α is as follows.

$$\alpha = (PvPf - 1_{+\Delta\theta}) \times Mg - (PmPf - 1_{+\Delta\theta}) \times V\rho$$

$$= 1_{+\Delta\theta} \times (V\rho - Mg) > 0$$

In this case also, the displacement of $+\Delta\theta$ is negated, i.e. the restoring force is produced. Therefore, the restoring force is produced when one of the disturbances $-\Delta\theta$ and $+\Delta\theta$ is produced in a case in which the capsule endoscope 1 is in point contact with the inner wall surface 2b of the body cavity upward in the vertical direction, and the inclined posture of the capsule endoscope 1 may be kept even more stably.

Figure 7:
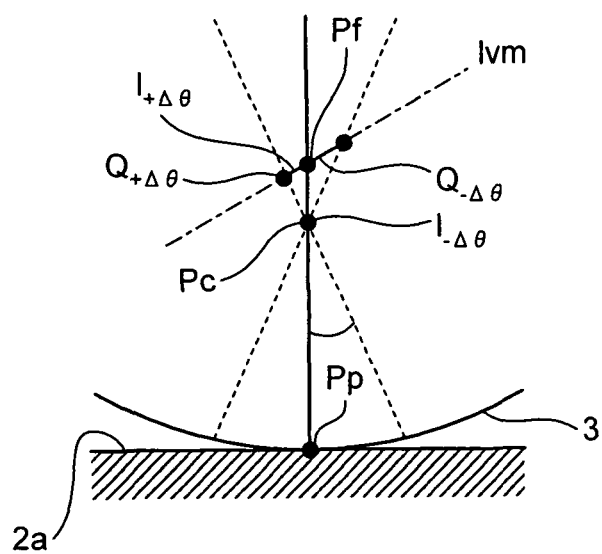
FIG. 7 is a diagram illustrating a size of a radius of curvature that hinders the stabilization of the capsule endoscope.

It should be noted that as shown in FIG. 7, when the point Pc is positioned between the points Pf and Pp, the displacement in moment α acts in a direction that amplifies the disturbance when the disturbance occurs, because the sign in $l_{-\Delta\theta}$ or $l_{+\Delta\theta}$ (direction) is inverted.

Also, as the radius of curvature PpPc becomes greater, a range in which the point Pf may be positioned becomes larger. In addition, when a condition for stabilization with respect to a disturbance in $\Delta\theta$ is satisfied by the points Pf, Pp, and Pc, values for $l_{-\Delta\theta}$ and $l_{+\Delta\theta}$ when the disturbance occurs become greater as the radius of curvature PpPc becomes greater, and accordingly, a value for the displacement in moment α becomes greater. In other words, when the disturbance occurs, the restoring force to restore the posture of the capsule endoscope 1 becomes greater, and thus, the capsule endoscope 1 becomes more stabilized.

Here, the capsule endoscope 1 as described above has the body cover 3b that is substantially hemispherical, and therefore the capsule endoscope 1 may come into point contact with the inner wall surface 2a or 2b of the body cavity. In the first embodiment according to the present invention, the capsule endoscope 1 may be provided with at least a protruding portion with which the capsule endoscope 1 may come into point contact with the inner wall surface 2a or 2b of the body cavity when the capsule endoscope 1 takes the inclined posture or the vertical posture.

Further, it is desirable that the acute angle formed by the meeting of the straight line connecting the point Pp and the point Pf with a center line of the long axis of the capsule endoscope 1 is equal to or smaller than 80°. At this time, the capsule endoscope 1 takes the inclined posture with the direction of its long axis forming an angle of 10° or greater with the horizontal direction. With this, the capsule endoscope 1 may easily receive the fluid resistance.

Figure 8:
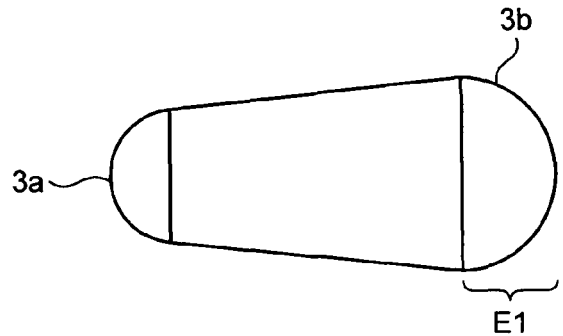
FIG. 8 is a diagram illustrating an example of a point contact portion of the capsule endoscope.

FIG. 8 shows a variant of an appearance of the capsule endoscope 1, and the radius of curvature for the body cover 3b is made greater than the radius of curvature for the tip cover 3a. As a result, the capsule endoscope shown in FIG. 8 has a larger radius of curvature for a point contact region E1, and it is possible to take the inclined posture or the vertical posture in a stable manner. Further, it is desirable that the radius of curvature for the point contact region E1 is greater than the diameter of the body cover.

Figure 9:
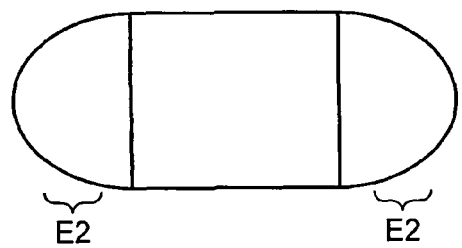
FIG. 9 is a diagram illustrating an example of a point contact portion of the capsule endoscope.

With the capsule endoscope shown in FIG. 9, a radius of curvature for a substantially hemispherical or substantially oval spherical shaped body that may be the body cover 3b is made greater than a diameter of a body part, and the part at which this radius of curvature is made greater is set to be a point contact region E2. Further, it is desirable that the radius of curvature for the point contact region E2 is greater than the diameter of the body cover.

Figure 10:
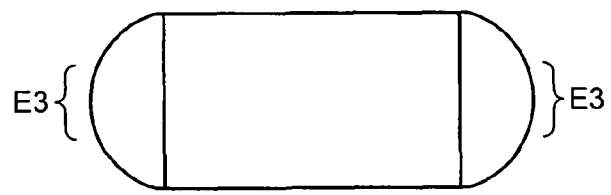
FIG. 10 is a diagram illustrating an example of a point contact portion of the capsule endoscope.

In addition, with the capsule endoscope shown in FIG. 10, a radius of curvature for a tip portion of a substantially hemispherical or substantially oval spherical shaped body that may be the body cover 3b is made greater than a diameter of a body part, and the part at which this radius of curvature is made greater is set to be a point contact region E3. This capsule endoscope is suitable to take the vertical posture.

Figure 11:
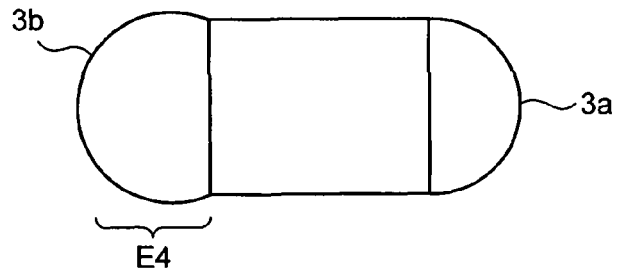
FIG. 11 is a diagram illustrating an example of a point contact portion of the capsule endoscope.

Further, with the capsule endoscope shown in FIG. 11, the body cover 3b of a substantially hemispherical shape which is greater than the diameter of the body portion is formed to obtain a point contact region E4 obtaining a large radius of curvature.

Figure 12:
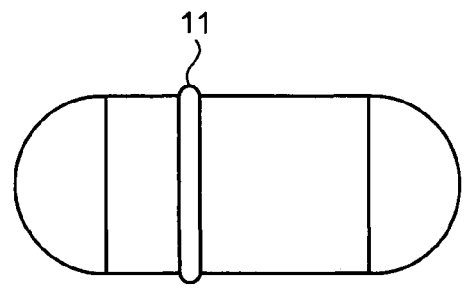
FIG. 12 is a diagram illustrating an example of a capsule housing of the capsule endoscope.
Figure 13:
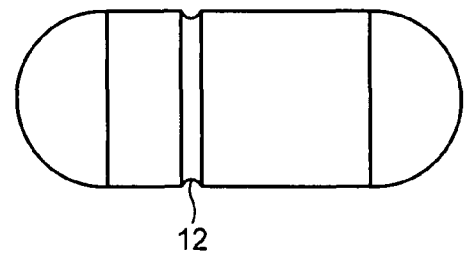
FIG. 13 is a diagram illustrating an example of a capsule housing of the capsule endoscope.

Moreover, in this first embodiment, as shown in FIG. 12 and FIG. 13, a projection 11 or a groove 12 may be formed on the body portion. This is because it does not affect the point contact between the capsule endoscope 1 and the inner wall surface 2a or 2b of the body cavity.

Figure 14:
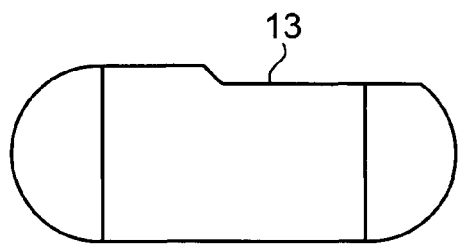
FIG. 14 is a diagram illustrating an example of a capsule housing of the capsule endoscope.
Figure 15:
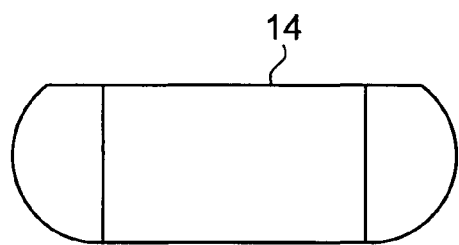
FIG. 15 is a diagram illustrating an example of a capsule housing of the capsule endoscope.

Further, a D-cut or the like may be formed at a part of the body portion and the tip cover 3a as shown in FIG. 14, and a D-cut or the like may be formed on a side in a long axis direction as shown in FIG. 15, because, in either case, the fact that a point contact region is formed or the D-cut is formed does not affect the point contact.

Figure 16:
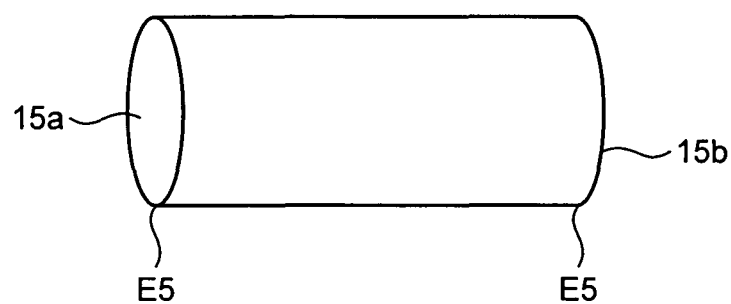
FIG. 16 is a diagram illustrating an example of a capsule housing of the capsule endoscope.
Figure 17:
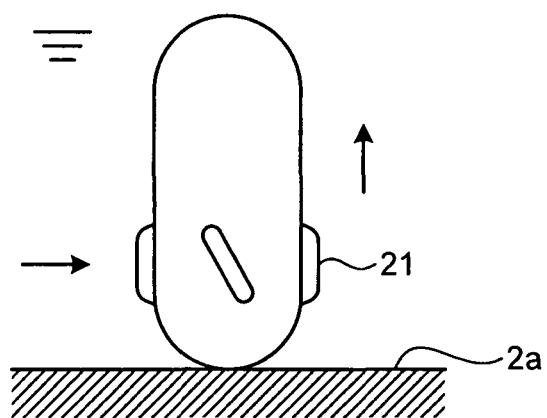
FIG. 17 shows a schematic construction of a second embodiment of the capsule endoscope according to the present invention.

In addition, in the above described first embodiment, the point contact portion is substantially hemispherical. However, it is not limited to such an example, and the capsule endoscope may be cylindrical, and peripheral portions of both end surfaces 15a and 15b may be set to be a point contact region E5 as shown in FIG. 16. In this case, smooth chamfering may be performed in order to make a radius of curvature of the point contact region E5 larger.

In this first embodiment, the fluid resistance due to the liquid flowing through the body cavity is made greater by having the capsule endoscope take the inclined posture or the vertical posture, and a contact resistance is made smaller by bringing the capsule endoscope into point contact with the inner wall surface of the body cavity. Accordingly, it is possible to have the capsule endoscope smoothly move along the flow of the liquid. In particular, the fluid resistance from the fast flow of the liquid in the proximity of the center of the body cavity is easily obtained, and therefore it is possible to move easily. Further, the capsule endoscope itself may keep the stable posture when the capsule endoscope moves or stops, and therefore, it is possible to stably obtain a desired image inside the subject. Moreover, it is possible to obtain the image in the center of the tube because the capsule may float easily, and accordingly the observability can be improved.

Figure 18:
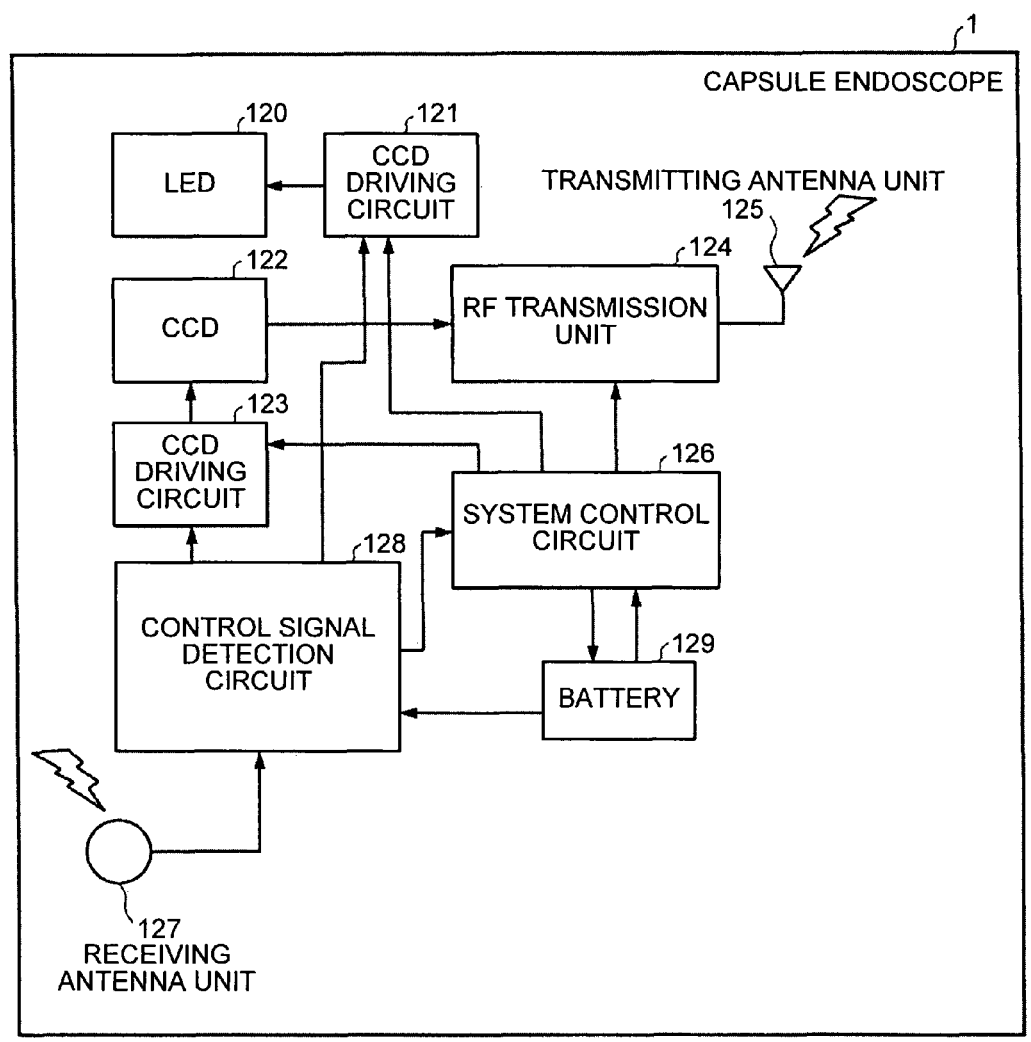
FIG. 18 is a block diagram showing a configuration of the capsule endoscope shown in FIG. 1.

It should be noted that, as shown in a block diagram of FIG. 18, the capsule endoscope 1 is provided with, for example, a light emitting diode (LED) 120 as irradiation means for irradiating a subject site in the body cavity in the subject, an LED driving circuit 121 as first drive means that controls a driving state of the LED 120, an imaging device (hereinafter referred to as CCD) 122, such as a CCD imager or a C-MOS imager, for example, as obtaining means that images an object in the body cavity that is light reflected from the region irradiated by the LED 120 (information in the subject), a CCD driving circuit 123 as first drive means that controls a driving state of the CCD 122, an RF transmission unit 124 that modulates image signals that have been imaged into RF signals, and a transmitting antenna unit 125 as wireless transmission means that wirelessly transmits the RF signals output from the RF transmission unit 124.

Moreover, the capsule endoscope 1 is provided with a system control circuit 126 that controls operations of the LED driving circuit 121, the CCD driving circuit 123, and the RF transmission unit 124, and with this, the capsule endoscope 1 may operate so that, while the capsule endoscope 1 is introduced in the subject, image data of the subject site irradiated by the LED 120 is obtained by the CCD 122.

Thereafter, the obtained image data is converted into the RF signals by the RF transmission unit 124, and transmitted outside the subject via the transmitting antenna unit 125.

Further, the capsule endoscope 1 is provided with a receiving antenna unit 127 as wireless reception means capable of receiving wireless signals transmitted from a communication device that is external to the subject and not shown in the figure, a control signal detection circuit 128 that detects control signals of a predetermined input level (level of intensity in reception, for example) out of the signals received by the receiving antenna unit 127, and a battery 129 that supplies power to the system control circuit 126 and the control signal detection circuit 128.

The control signal detection circuit 128 detects contents of the control signals, and outputs the control signals, as necessary, to the LED driving circuit 121, the CCD driving circuit 123, and the system control circuit 126. The system control circuit 126 has a function of distributing the driving power supplied from the battery 129 to the other components (means for performing functions).

Figure 19:
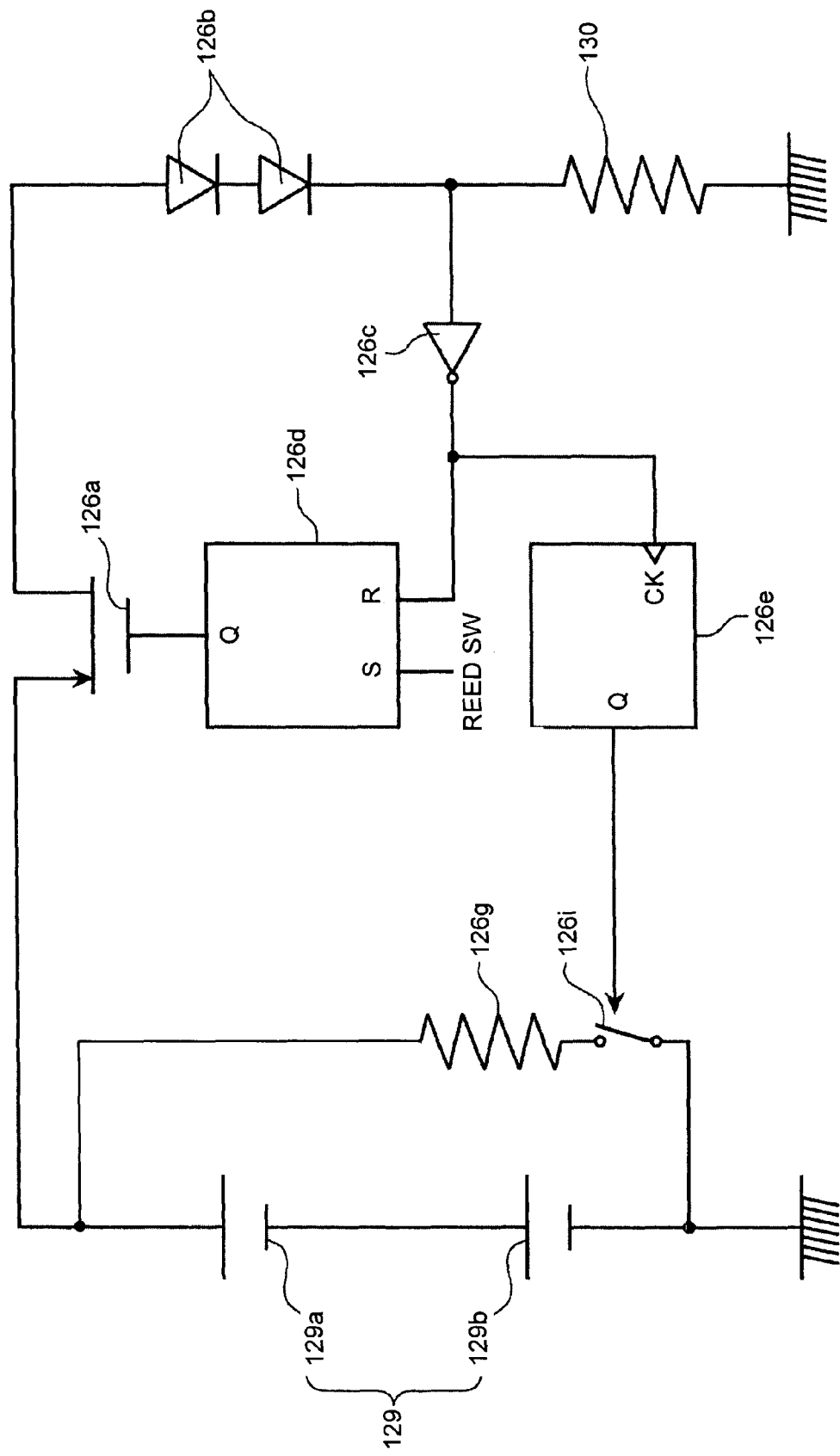
FIG. 19 is a circuit diagram showing a configuration of a system control circuit shown in FIG. 18.

Moreover, FIG. 19 is a circuit diagram showing a circuit configuration of the system control circuit 126. In FIG. 19, the battery 129 is constituted by one or more (two in first embodiment), for example, button type silver oxide batteries 129a and 129b.

The system control circuit 126 is provided with a FET (field effect transistor) 126a whose source terminal is connected to the battery 129, a diode 126b connected to a drain terminal of the FET 126a, a NOT circuit 126c connected to an output terminal of the diode 126b, and a flip flop 126d that is reset (R) by an output from the NOT circuit 126c and outputs (Q) to a gate terminal of the FET 126a.

The output from the diode 126b is connected to a in-capsule function performing circuit 130, and the flip flop 126d is set (S) by an input from a reed switch that detects an external magnetizing field.

It should be noted that in this first embodiment, a switching element, for example, may be used instead of a transistor such as an FET. Further, in this first embodiment, an imaging function, a illumination function, and a wireless function (partial) provided for the capsule endoscope 1 are referred to collectively as function performing means for performing predetermined functions. Specifically, the components excluding the system control circuit 126, the receiving antenna unit 127, and the control signal detection circuit 128 are included in the function performing means for performing the predetermined functions, and also referred to as the in-capsule function performing circuit 130 as needed.

Moreover, the system control circuit 126 is provided with a flip flop 126e to which an output of the NOT circuit 126c is input (CK), a resistance 126g connectable to the button type batteries 129a and 129b, and a switching element 126i.

An operation of the switching element 126i is controlled by the NOT circuit 126c and the flip flop 126e so as to be in an off state while the button type batteries 129a and 129b supplies the driving power to the in-capsule function performing circuit 130, and switched to an on state when the supply of the driving power to the in-capsule function performing circuit 130 stops.

Specifically, the switching element 126i is switched to the on state by the output (Q) from the flip flop 126e, and connects the button type batteries 129a and 129b with the resistance 126g to have the power charged in the button type batteries 129a and 129b be exhausted.

Next, an operation of the capsule endoscope 1 is described using the circuit diagram FIG. 19. In FIG. 19, for example, the capsule endoscope 1 before introduced into the subject includes a reed switch therein that can be turned on and off by an external magnetizing field, and stored in a package that includes a permanent magnet for supplying the external magnetizing field. In this state, the capsule endoscope 1 is not driven.

Next, when it is taken in, as the capsule endoscope 1 is taken out of the package, the capsule endoscope 1 is separated from the permanent magnet of the package, and the capsule endoscope 1 is not affected by the magnetic force, and the flip flop 126d is set (S) by the input from the reed switch. Once set, the flip flop 126d outputs (Q) to the gate terminal of the FET 126a, and a current flows between the source and drain terminals of the FET 126a by this output (Q), and the power from the button type batteries 129a and 129b is supplied to the in-capsule function performing circuit 130 via the diode 126b.

Here, when a voltage supplied from the button type batteries 129a and 129b is A, and voltages consumed at the FET 126a and the diode are respectively B and C, a voltage to be supplied to the in-capsule function performing circuit 130 is A−(B+C)=X. Further, the NOT circuit 126c is set with a midpoint potential Y as a threshold, and when the voltage X is greater than the midpoint potential Y, i.e. (voltage X)>(midpoint potential Y), it is not output from the NOT circuit 126c, and the switch element 126i is switched to the off state.

Moreover, when the voltage X is equal to or smaller than the midpoint potential Y, i.e. (voltage X)≤(midpoint potential Y), the flip flop 126d is reset by the output from the NOT circuit 126c, and the output from the NOT circuit 126c is input to the flip flop 126e. Then, when the flip flop 126d is reset, the current does not flow between the source and drain terminals, and the driving power is not supplied to the in-capsule function performing circuit 130.

Furthermore, when the output from the NOT circuit 126c is input, the flip flop 126e outputs (Q), and switches the switch element 126i to the on state.

The button type batteries 129a and 129b and the resistance 126g are connected by this switching operation, and the power charged in the button type batteries 129a and 129b is exhausted by the resistance 126e.

Second Embodiment

Next, a second embodiment according to the present invention is described. In the above described first embodiment, the mobility and the flotation of the capsule endoscope are facilitated by increasing the fluid resistance that the capsule endoscope itself receives. In this second embodiment, a function of further increasing the fluid resistance is provided for the capsule endoscope.

FIG. 19 is a circuit diagram showing a schematic configuration of the capsule endoscope of the second embodiment according to the present invention. The capsule endoscope shown in FIG. 19 is in point contact with the inner wall surface 2a of the body cavity downward in the vertical direction, and takes the vertical posture in which the long axis aligns with the vertical direction. This capsule endoscope is provided with a fin 21 around the body portion for turning the capsule endoscope about the long axis in response to the flow of the liquid 7.

In addition that the capsule endoscope as a whole increases the fluid resistance in response to the flow of the liquid, this capsule endoscope is configured to provide lift by the fin 21 with help of the fluid resistance so that the capsule endoscope is separated away from the inner wall surface 2a of the body cavity. With this configuration, the capsule endoscope becomes easier to move in response to the flow of the liquid.

Figure 20:
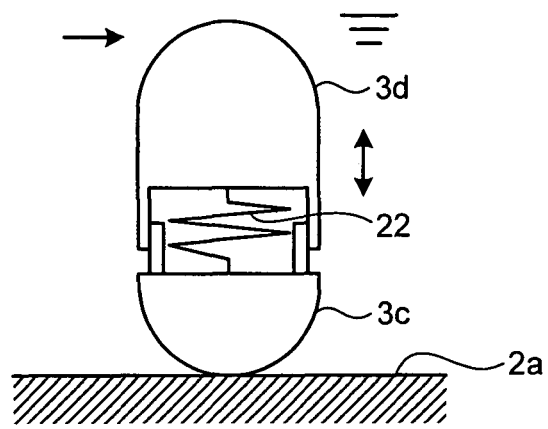
FIG. 20 shows a schematic construction of a first variant of the second embodiment of the capsule endoscope according to the present invention.

Further, FIG. 20 shows a schematic construction of the capsule endoscope as a variant of the second embodiment of according to the present invention. The capsule endoscope shown in FIG. 20 is separated into a partial housing 3c having the point contact portion and a housing body 3d that is on the tip cover side, and the partial housing 3c and the housing body 3d are connected by a spring member 22 as a resilient member. In addition, this capsule endoscope takes the vertical posture similarly to the capsule endoscope shown in FIG. 19.

In addition that this capsule endoscope receives the fluid resistance on the entire capsule endoscope, the housing body 3d moves, for example, downward in the vertical direction by the fluid resistance, energy increases in compression of the spring member 22, then the housing body 3d moves upward in the vertical direction by repulsive force due to extension of the spring member 22, and the partial housing 3c moves upward in the vertical direction by inertia force at this time, thereby releasing the point contact state and thus improving the mobility and the flotation of the capsule endoscope.

Figure 21:
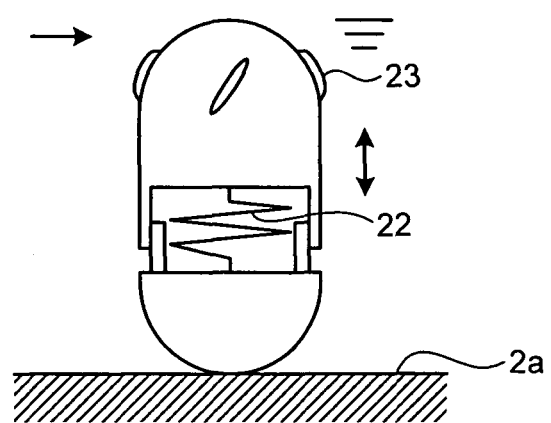
FIG. 21 shows a schematic construction of a second variant of the second embodiment of the capsule endoscope according to the present invention.

FIG. 21 shows a construction combining the above configurations shown in FIG. 19 and FIG. 20. However, a fin 23 does not provide lift upward in the vertical direction, but downward in the vertical direction. Consequently, it is possible to further increase the compression of the spring member 22, and the release of the point contact state of the capsule endoscope is even more facilitated.

In this second embodiment, the fluid resistance is further increased in addition to the fluid resistance that the capsule endoscope itself receives to release the point contact state, the mobility and the flotation of the capsule endoscope along the flow of the fluid are further improved.

Third Embodiment

Next, a third embodiment according to the present invention is described. In the first and the second embodiments, the capsule endoscope keeps the inclined posture or the vertical posture while maintaining the point contact state with the inner wall surface of the body cavity. However, in this third embodiment, the capsule endoscope is configured to obtain a stable image in the body cavity in a direction of the tube axis utilizing the stable inclined posture.

Figure 22:
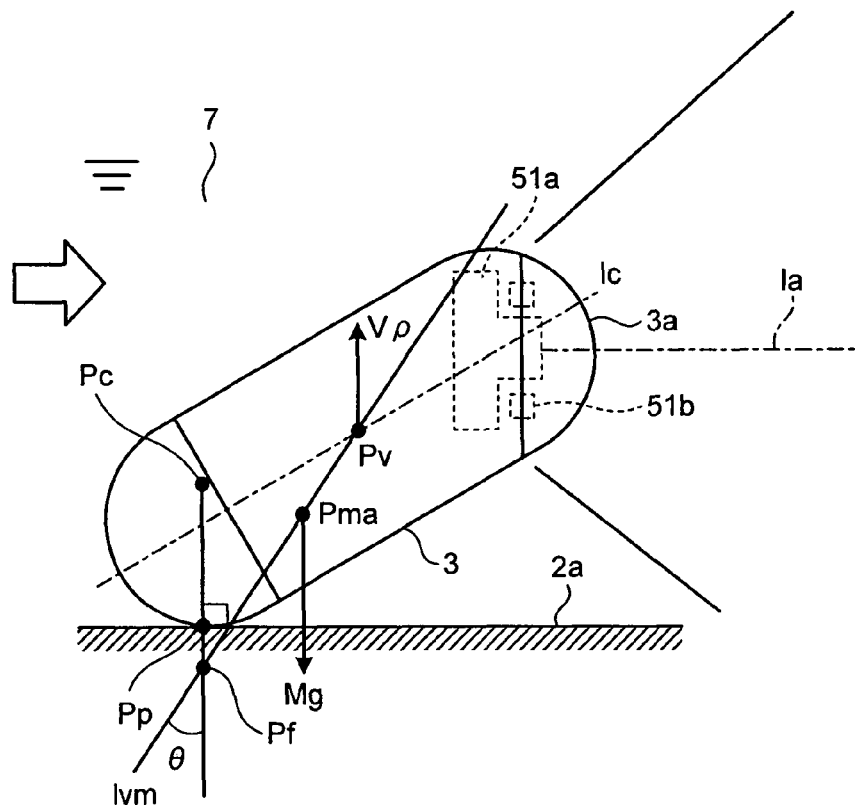
FIG. 22 shows a schematic construction of a third embodiment of the capsule endoscope according to the present invention.

FIG. 22 shows a schematic construction of the capsule endoscope of the third embodiment according to the present invention. In this capsule endoscope, the center of gravity Pma is provided at an eccentric position from a long axis center line 1c, and furthermore this capsule endoscope is provided so that an optical axis 1a of the imaging optical system provided on the tip cover side and including an imaging unit 51a and an illumination unit 51b is at an angle with respect to the long axis center line 1c of the capsule endoscope. It should be noted that the optical axis 1a is provided at an angle with respect to the long axis in a direction of eccentricity of the center of gravity, centering a straight line perpendicular to a plane including the long axis and the center of gravity.

This capsule endoscope takes the inclined posture in which the direction of eccentricity of the center of gravity Pma from the long axis center line 1c always faces downward in the vertical direction. Accordingly, the optical axis 1a of the imaging optical system is directed always at the same angle to the surroundings from the inner wall surface 2a of the body cavity downward in the vertical direction. Moreover, because the capsule endoscope as a whole, similarly to the first embodiment, easily receives the fluid resistance, this capsule endoscope is directed toward the direction of the flow of the fluid, i.e. downstream. As a result, this capsule endoscope is allowed to obtain an image in the body cavity always substantially at the same angle and facing the downstream of the fluid, as well as determination of the obtained image in the body cavity becomes easier because the capsule endoscope does not turn about the long axis. Further, although not shown, when the direction of angle of the optical axis 1a to the long axis center line is opposite to the direction of eccentricity, the same effect may be obtained in a situation in which the body cavity runs in the vertical direction.

Figure 23:
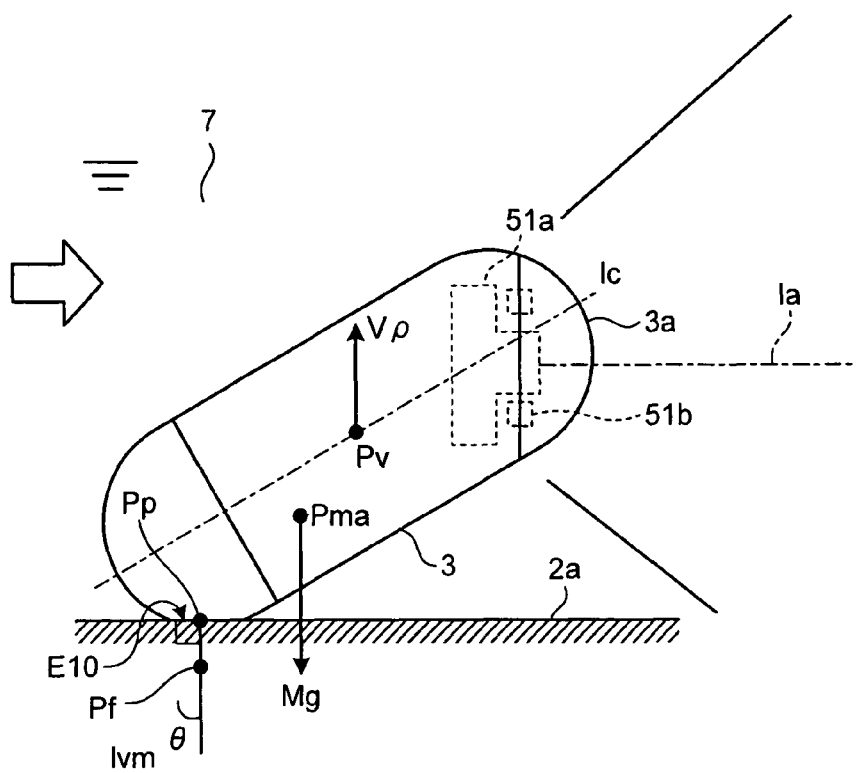
FIG. 23 shows a schematic construction of a first variant of the third embodiment of the capsule endoscope according to the present invention.

Although the capsule endoscope shown in FIG. 22 and the inner wall surface 2a of the body cavity are in point contact, this point contact may be in plane contact as shown in FIG. 23. However, the capsule endoscope takes the inclined posture. In other words, the capsule endoscope is provided with a flat region E10 at a portion on the side of the body cover. Other configuration is the same as the capsule endoscope shown in FIG. 22. However, the portion where the flat region E10 is provided is provided in the direction of eccentricity of the center of gravity Pma from the long axis center line 1c. In the capsule endoscope shown in FIG. 23, because the flat region E10 is in plane contact with the inner wall surface 2a of the body cavity, the inclined posture is stabilized and it is possible to obtain a desired image in the body cavity.

Further, although not shown, it is possible to achieve the same effect by configuring such that the body cover portion of the capsule endoscope includes a flat portion of a circular truncated cone, and a bus line portion thereof is brought into line contact with an intestine wall, and the desired image of the body cavity may be stably obtained. In addition, because the intestine wall is brought into line contact with the capsule endoscope as well as because the capsule endoscope takes the inclined posture, similarly to the point contact state, the capsule endoscope 1 receives the fluid resistance easily.

Figure 24:
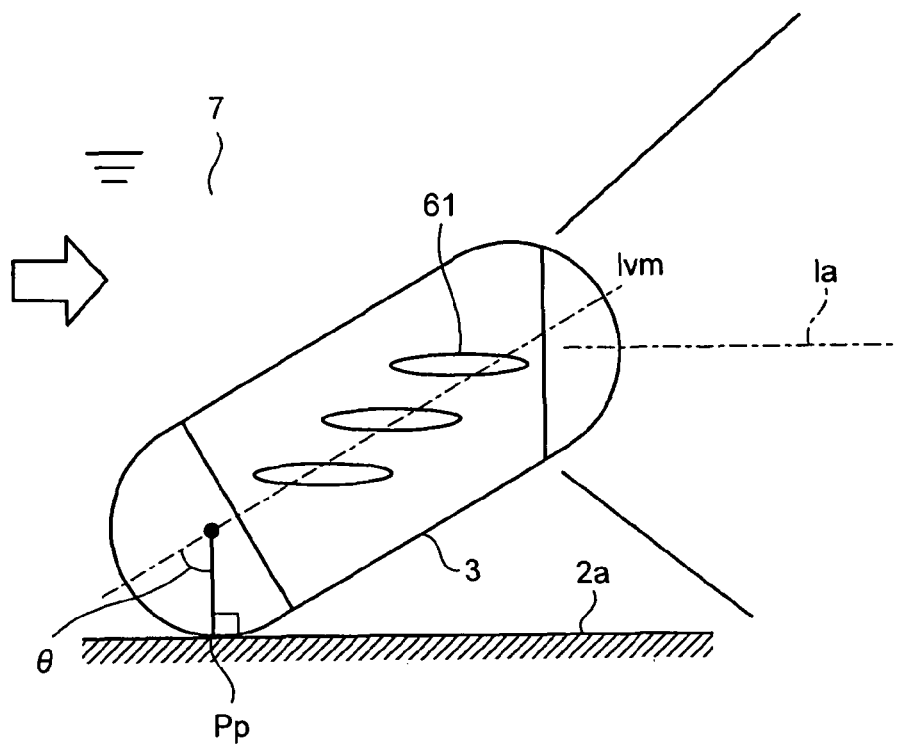
FIG. 24 is a diagram illustrating a configuration of the capsule endoscope shown in FIG. 22 provided with a fin for rectification.
Figure 25:
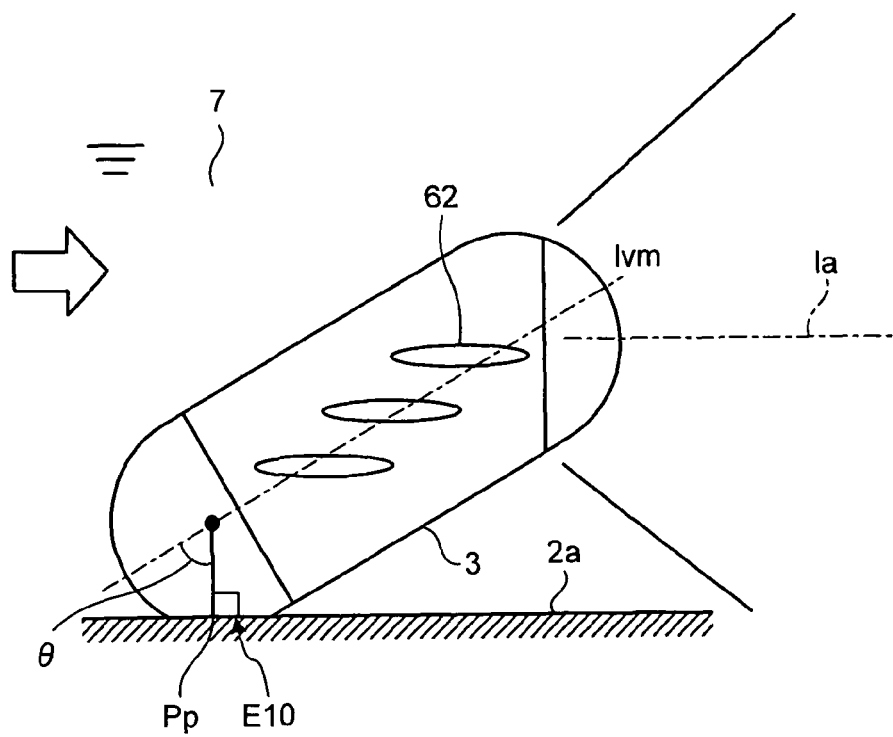
FIG. 25 is a diagram illustrating a configuration of the capsule endoscope shown in FIG. 23 provided with a fin for rectification.

Moreover, as shown in FIG. 24 and FIG. 25, fins 61 and 62 that rectify the flow of the fluid 7 may be provided on outer surfaces of the capsule endoscopes shown in FIG. 22 and FIG. 23, respectively. The fins 61 and 62, when the capsule endoscope takes the inclined posture, rectifies the flow along the flow direction of the fluid 7, and ensures the maintenance of the inclined posture.

Figure 26:
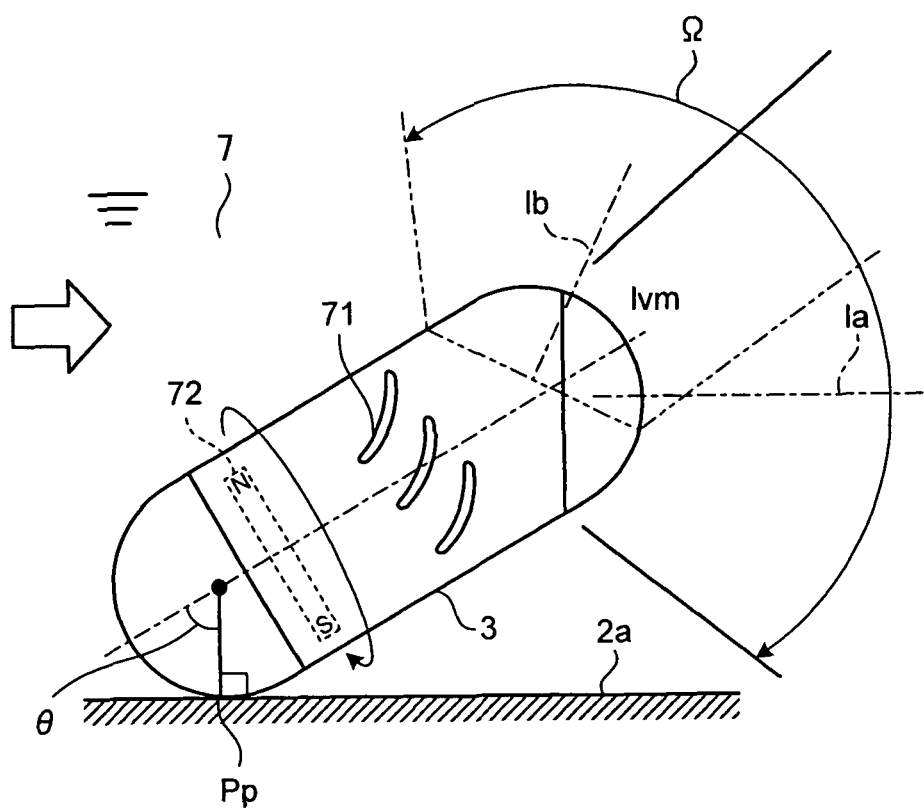
FIG. 26 is a diagram illustrating a configuration of the capsule endoscope shown in FIG. 22 provided with a fin for turning around.

In addition, a fin 71 as shown in FIG. 26 may be provided so that the capsule endoscope turns about the long axis center line in response to the flow of the fluid 7. With the turning of the capsule endoscope about the long axis center line, the optical axis 1a rotates and a solid angle Ω of a substantial imaging area increases, thereby obtaining a wide area of the image in the body cavity.

It should be noted that, as shown in FIG. 26, it is possible to provide a magnet 72 that perpendicularly intersects with the long axis center line to apply a rotating magnetic field from outside, thereby having the capsule endoscope turn.

In this third embodiment, because the center of gravity is decentered so that the capsule endoscope does not turn about the long axis center line when the capsule endoscope takes the inclined posture, it is possible to set the optical axis of the imaging optical system at an angle with the long axis center line, and the image in the body cavity in the desired direction may be obtained stably.

Although, in the first to the third embodiments, the specific gravity of the capsule endoscope is explained to be slightly smaller or larger than the specific gravity of the liquid, it is not limited to these examples. The relation between the specific gravity of the capsule endoscope and the specific gravity of the liquid may be set so that capsule endoscope may move easily, considering the fluid resistance that the capsule endoscope receives and the contact state such as friction with the wall surface.

Further, not limited to the capsule endoscope, the same effect can be obtained with capsule medical apparatuses such as an ultrasonic capsule that is provided with a ultrasonic inspection device and obtains an ultrasonic image in the subject and a sensor capsule provided with a sensor for detecting a specific substance, PH, or a pressure in the subject. Here, because the ultrasonic capsule easily floats by the flow in the body cavity, it is possible to obtain the ultrasonic image in the center of the body cavity, thereby improving the observability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus, comprising a capsule housing having a protruded portion on a longitudinal axis at one end, wherein
    the protruded portion is formed so that an outer surface of the protruded portion intersects perpendicularly with a first straight line,
    the first straight line substantially intersects with a second straight line connecting a center of buoyancy and a center of gravity when the capsule housing is in liquid in a body cavity,
    the first straight line and the second straight line substantially intersect at a balance point where a buoyant moment produced by buoyancy acting on the center of buoyancy and gravitational moment produced by gravity acting on the center of gravity are substantially balanced,
    an acute angle is formed by the first straight line and the second straight line,
    wherein either the balance point is positioned between an intersection of the first straight line and the outer surface of the protruded portion, and a center of curvature of the protruded portion at the intersection, the center of curvature being on a plane including the balance point, the intersection, and the center of buoyancy, or the intersection is positioned between the balance point and the center of curvature, and
    the capsule medical apparatus is configured to be in point contact with an inner wall of the body cavity at the intersection.

2. The capsule medical apparatus according to claim 1, wherein specific gravity of the capsule medical apparatus is a proximity value of specific gravity of the fluid.

3. The capsule medical apparatus according to claim 1, wherein the second straight line is the longitudinal axis of the capsule medical apparatus, and
    the acute angle formed by the first straight line that intersects perpendicularly with the outer surface of the protruded portion and the longitudinal axis is equal to or smaller than 80 degrees.

4. The capsule medical apparatus according to claim 1, comprising a fluid resistance portion having a resistance to the fluid that flows in the body cavity.

5. The capsule medical apparatus according to claim 4, wherein the fluid resistance portion is a fin provided on a surface of the capsule housing, and capable of producing a force in a direction to move away from an inner wall surface of the body cavity in response to a flow of the fluid.

6. The capsule medical apparatus according to claim 4, wherein the fluid resistance portion is a fin that produces a rotational motion about the longitudinal axis.

7. The capsule medical apparatus according to claim 4, wherein the capsule housing includes a first housing unit having an intersection of the first straight line that intersects perpendicularly with the outer surface of the protruded portion and the protruded portion, and a second housing unit having the fluid resistance portion, the first housing unit and the second housing unit are connected via a resilient member, energy which the fluid resistance portion receives is accumulated at the resilient member, and the capsule medical apparatus is separated from the inner wall surface of the body cavity using the accumulated energy.

8. The capsule medical apparatus according to claim 1, wherein both ends of the capsule housing in a longitudinal axis direction form a dome shape.

9. The capsule medical apparatus according to claim 1, wherein the capsule housing is provided with an imaging system on the other end of the protruded portion, the imaging system imaging an image in the body cavity.

10. The capsule medical apparatus according to claim 9, wherein
    the center of gravity is positioned at an eccentric position from the longitudinal axis of the capsule housing, and
    an imaging axis of the imaging system is provided at an angle with the longitudinal axis centering around a straight line perpendicular to a plane including the longitudinal axis and the center of gravity.

11. The capsule medical apparatus according to claim 10, comprising a rectifying portion that is provided on a surface of the capsule housing and rectifies a flow of the liquid.

12. The capsule medical apparatus according to claim 10, comprising a fluid resistance portion that is provided on a surface of the capsule housing and has the capsule medical apparatus turn about the longitudinal axis in response to a flow of the liquid.

13. The capsule medical apparatus according to claim 10, comprising a magnetic body, within the capsule housing, having magnetism that is substantially perpendicular to the longitudinal axis, wherein
    the capsule housing turns about the longitudinal axis by rotating magnetic field applied from outside.

14. The capsule medical apparatus according to claim 1, wherein the protruded portion includes a flat portion, an intersection of the first straight line that intersects perpendicularly with the outer surface of the protruded portion and the protruded portion is at the flat portion.

15. The capsule medical apparatus according to claim 1, wherein the protruded portion includes a circular truncated cone plane portion, an intersection of the first straight line that intersects perpendicularly with the outer surface of the protruded portion and the protruded portion is at the circular truncated cone plane portion.

16. The capsule medical apparatus according to claim 1, wherein the capsule housing includes a body portion that is in a substantial cylindrical shape and whose center axis is parallel to the longitudinal axis, and
    a radius of curvature of the protruded portion at an intersection of the first straight line that intersects perpendicularly with the outer surface of the protruded portion and the protruded portion is greater than a diameter of the substantial cylindrical shape.

17. The capsule medical apparatus according to claim 16, wherein
    the protruded portion has a substantially oval spherical protruded shape that is connected to the substantial cylindrical shape, and
    the radius of curvature of the protruded portion increases gradually toward an end in a direction of the longitudinal axis.

18. The capsule medical apparatus according to claim 16, wherein the protruded portion has a substantially oval spherical protruded shape that is connected to the cylindrical shape, and the radius of curvature of the protruded portion decreases gradually toward an end in a direction of the longitudinal axis.

19. A capsule medical apparatus, comprising a point contact portion having a protruded shape on a circumference of one end of a capsule housing having a body in a substantially cylindrical shape, wherein moment of a center of buoyancy and moment of a center of gravity are balanced at a balance point which is an intersection of a first straight line as a vertical line passing through the point contact portion and a second straight line passing through the center of buoyancy and the center of gravity of the capsule housing, so that the capsule medical apparatus takes a desired posture such that the capsule medical apparatus is configured to be brought into point contact with an inner wall surface of a body cavity at the point contact portion in liquid introduced into the body cavity, an acute angle is formed by the first straight line and the second straight line, and either the balance point is positioned between the point contact portion and a center of curvature of the point contact portion, or the point contact portion is positioned between the balance point and the center of curvature of the point contact portion.

20. The capsule medical apparatus according to claim 19, wherein the second straight line is a longitudinal axis of the capsule medical apparatus, and the acute angle formed by the vertical line that passes the point contact portion and the longitudinal axis is equal to or smaller than 80 degrees.

* * * * *